United States Patent [19]
Ehrlich et al.

[11] Patent Number: 5,443,793
[45] Date of Patent: Aug. 22, 1995

[54] ATMOSPHERIC CONTAMINANT DETECTOR

[75] Inventors: John J. Ehrlich; Wayne E. Davenport, both of Huntsville; Travis S. Taylor, Somerville, all of Ala.

[73] Assignee: The United States of America as represented by the Secretary of the Army, Washington, D.C.

[21] Appl. No.: 146,842

[22] Filed: Nov. 5, 1993

[51] Int. Cl.⁶ .......................... G01N 21/63; G01J 3/28
[52] U.S. Cl. ........................................ 422/83; 422/91;
422/94; 250/343; 250/345; 250/372; 250/374;
86/1.1
[58] Field of Search ........................... 422/83, 91, 94;
250/345, 343, 372, 374; 356/427; 86/1.1;
33/267, DIG. 21

[56] References Cited

U.S. PATENT DOCUMENTS

| | | | |
|---|---|---|---|
| 3,761,715 | 9/1973 | Menzies | 250/338 |
| 3,766,380 | 10/1973 | Menzies | 250/343 |
| 3,891,848 | 6/1975 | Fletcher et al. | 250/345 |
| 4,127,329 | 11/1978 | Chang et al. | 356/301 |
| 4,200,608 | 4/1980 | Croomes et al. | 422/97 |
| 4,516,858 | 5/1985 | Gelbwachs | 356/437 |
| 4,529,489 | 7/1985 | McDonald et al. | 204/158 |
| 5,015,855 | 5/1991 | Braunuce et al. | 250/337 |
| 5,041,734 | 8/1991 | Tetzlaft et al. | 250/484.1 |
| 5,241,179 | 8/1993 | Carrieri | 250/341 |

OTHER PUBLICATIONS

Basic Principles of Organic Chemistry, Second Edition, W. A. Benjamin, Inc., Roberts and Caserio, pp. 960, 961.
Basic Principles of Organic Chemistry, Second Edition, W. A. Benjamin, Inc., Roberts and Caserio, pp. 1372–1375.

*Primary Examiner*—Robert J. Warden
*Assistant Examiner*—N. Bhat
*Attorney, Agent, or Firm*—Anthony T. Lane; Hugh P. Nicholson; Freddie M. Bush

[57] ABSTRACT

This invention provides a means for detecting local atmospheric contaminants from safe distances. The invention means of a detector system comprise a pulsed laser, a sensitive photo-detector, various optical filters, and necessary digital control circuitry. The detector system employs laser technology in combination with a sensitive photo-detector to achieve detection of any hazardous gas elements or other pollutants remotely located from personnel who may subsequently be exposed. In operation, a pulsed laser or a tunable dye laser is employed as an excitation source for the contaminant or pollutant to achieve excitation of the contaminant or pollutant. When the excited molecule of the contaminant or pollutant returns to ground-state it emits a photon at a given (measurable) frequency. A sensitive photo-detector is filtered to permit detection of only the frequency at which a harmful gas (as an example of a contaminant or pollutant) fluoresces. Various filters can be utilized at once to enable the detector to detect more than one pollutant at a time. A timer in the system determines time elapse from the time the laser is pulsed to the time a photon is detected, the location of the gas pollutant can then be determined. Similarly, by relating distance and intensity of fluorescence via the detector, the density of the gas pollutant in the local atmosphere can be determined. The entire system is controlled by simple compact digital technology.

3 Claims, 1 Drawing Sheet

ATMOSPHERIC CONTAMINANT DETECTOR

DEDICATORY CLAUSE

The invention described herein may be manufactured, used, and licensed by or for the Government for governmental purposes without the payment to us of any royalties thereon.

BACKGROUND OF THE INVENTION

The detection of gases, fumes, and radiation is essential for monitoring conditions relative to the safety of personnel in an area of exposure. The detection mechanisms encompass several disciplines. As an example, a chemical reaction can take place between the elements desired to be detected and a change is measured. The means for detection can be based on catalytic decomposition of fumes after coming in contact with the active ingredient of the detector. As an example, the active ingredient of one detector is deposited within and upon a ceramic pellet. The pellet is fitted with a thermal responsive means responsive to heat generated. An output signal proportional to the generated heat can be interpreted by a balanced electronic bridge. This described detector is a detector for fumes of hydrazine and its derivatives as disclosed and claimed in a commonly assigned U.S. Pat. 4,200,608 issued on Apr. 29, 1980 to Edgar F. Croomes et al.

Detectors for radiation can be in the form of a pen shaped article containing a charged tube. Any exposure to ionizing radiation can effect a discharge of a fully charged pen which is proportional to the radiation to which the person wearing the pen is exposed. The pen can be measured with respect to discharged values which can be equated to radiation exposure values. This type pen is worn by employees who are subjected to any ionizing type radiation such as x-ray in combination with a fluorescent screen.

The above descriptions provide examples of typical detectors where detection is made in the proximity of the personnel or in a fixed storage area.

There are many needs for a system that can detect atmospheric pollutants from a distance by remotely located detectors. As an example, it would be beneficial for foot soldiers to know if a battle field has had harmful gases released on it before they enter that battlefield. Present systems require that the hazardous gas detector be exposed to the gas in order to function. This means that the soldier carrying the detector is exposed to the gas and may have only a few seconds to take evasive actions.

An object of this invention is to provide a detector system which can detect harmful atmospheric pollutants before personnel are actually being exposed to the harmful atmospheric pollutants.

A further object of this invention is to provide a detector system which employs laser technology in combination with a sensitive photo-detector to achieve detection of any hazardous gas elements or other pollutants remotely located from personnel who may subsequently be exposed.

SUMMARY OF THE INVENTION

The atmospheric contaminant detector of this invention employs a laser selected from a tripled Nd:Yag laser, a pulsed laser, a CW tunable laser, a $N_2$ discharge laser or a tunable dye laser as an excitation source for the contaminant or pollutant to achieve excitation of the contaminant or pollutant. When the excited molecule of the contaminant or pollutant returns to ground state, it emits a photon at a given (measurable) frequency. A sensitive photo-detector is filtered to detect only the frequency at which a harmful gas (as an example of a contaminant or pollutant) fluoresces. Various notch filters can be utilized at once to enable the detector to detect more than one pollutant at a time. A timer in the system determines time elapse from the time the laser is pulsed to the time a photon is detected; the location of the gas can then be determined. By determining the distance that the harmful gas is from the detector and by measuring the intensity of the fluorescence via the detector, the density of the gas in the local atmosphere can be determined. The entire system is controlled by simple compact digital technology.

BRIEF OF THE DESCRIPTION OF THE DRAWINGS

The Figures of the Drawing depicts an atmosphere contaminant detector in FIG. 1 prior to laser excitation of atmospheric contaminant molecules; and FIG. 2 depicts the same atmospheric contaminant detector after laser excitation of atmospheric contaminant molecules.

DESCRIPTION OF THE PREFERRED EMBODIMENT

Figure 1:
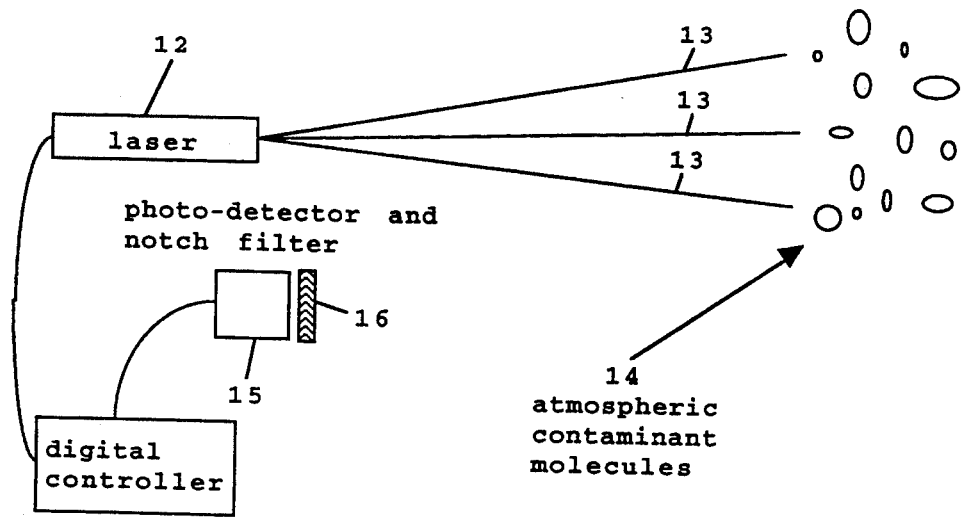
Figure 2:
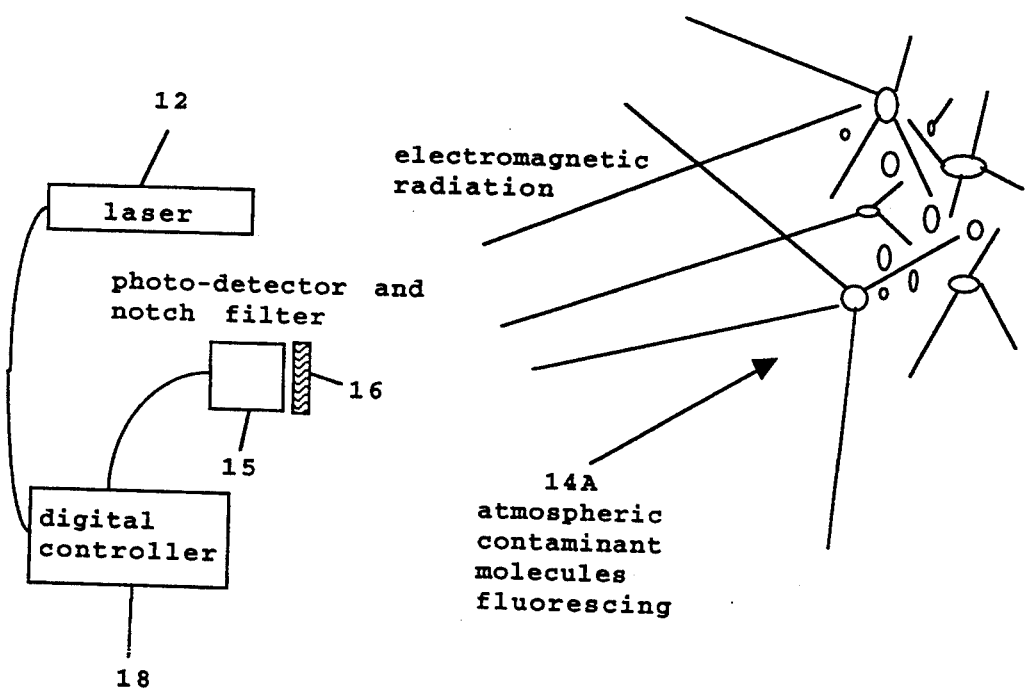

The atmospheric contaminant detector system 10 of this invention is illustrated in FIGS. 1 and 2. FIG. 1 depicts a pulsed laser source 12 selected from a tripled Nd:Yag, $N_2$ discharge, or a tunable dye laser. FIG. 1 illustrates atmospheric contaminant molecules 14 prior to receiving the pulses or laser radiation 13. FIG. 2 depicts the pulsed laser source after cessation of irradiation and the subsequent fluorescence of contaminant molecules 14A which is defined as the emission of light or of other electromagnetic radiation by a material exposed to another type of radiation or to a beam of particles, with the luminescence ceasing within about $10^{-8}$ seconds after irradiation is stopped.

In operation in its environment of usefulness, a laser 12 is fired in pulses across a battlefield. If the battlefield is contaminated with harmful gases, the laser pulses 13 hits the gas molecule and excites it. When the excited molecule returns to ground state, it emits electromagnetic radiation or photons at a given (measurable) frequency. The photo-detector 15 is filtered by notch filter 16 to detect only the frequency at which the harmful gas fluoresces. Thus, if the photo-detector detects a characteristic photon which would be emitted after irradiation is stopped, the harmful gas is identified as being present. Various filters (of the type filter 16) can be utilized at once to enable the photo-detector to detect more than one pollutant or harmful gas at a time. Also, by placing a simple timer (not shown) in the system that measures the time a laser is pulsed to the time a photon is detected, the location of the harmful gas can be determined. By knowing the distance that the gas is from the detector and by measuring the intensity of the fluorescence via the detector, the density of the gas in the local atmosphere can be determined. The entire system 10 is controlled by a simple, compact digital controller 18.

The electromagnetic radiation spectra of particular interest to the atmospheric contaminant detector disclosed herein relates to the spectrum ultraviolet (UV), visible and infrared (IR, near, middle, and far) shown in Table I below.

TABLE I

SPECTRUM UV VISIBLE AND IR

| Spectrum | Range Wavelength in nm | Range Wavelength in $\mu$ |
|---|---|---|
| UV | 20–380 | 0.02–0.38 |
| Visible | 397–723 | 0.397–0.723 |
| IR (near) | 750–1500 | 0.750–1.5 |
| IR (middle) | 1500–10,000 | 1.5–10 |
| IR (far) | 10,000–1,000,000 | 10–1,000 |

As noted in the above table, the wavelength ranges are in nanometers (nm) and in microns ($\mu$) which is useful in practicing this invention in the selection of laser wavelength lines which are absorbed by various compounds classified as atmospheric contaminants. Chemical agents or nerve agents, classified as organophosphorus chemical agents which would be atmospheric contaminants of the worst kind, are discussed below along with a method for decomposing them by laser irradiation.

The teachings of a commonly assigned U.S. Pat. No. 4,529,489, issued on Jul. 16, 1985 to Joseph K. McDonald et al is devoted to using a CW tunable laser in a laser photochemical decomposition method to achieve decomposition of a compound of high toxicity to relatively non-toxic decomposition products. This patent identifies and provides the chemical structure for nerve agents which are also organophosphorus chemical agents which contain a characteristic C—O—P group. These organophosphorus chemical agents when irradiated with a predetermined power level from about 10 to about 150 w/cm$^2$ for a predetermined time period effects cleavage of the C—O bond. This method is highly selective for cleavage of the C—O bond rather than cleavage of the P—O bond, and in the presence of air, the method requires low power levels of the CO$_2$ laser for rapid and complete dissociation of the organophosphorus chemical to relatively non-toxic decomposition products.

In order to provide an understanding of radiation and how compounds react to absorbed radiation, a discussion is now provided to focus attention to the technical aspects of the atmospheric contaminant detector of this invention.

According to the Franck-Condon principle, the processes wherein all the energy of the light quantum is taken up in excitation of an electron to a high-energy, usually antibonding, orbital, occur more rapidly than the vibration of atoms in their bonds. The short transition time of an electron between ground and excited states is in complete contrast to what happens during absorption of a quantum of lower frequency of electromagnetic radiation such as radio-frequency energy in nmr spectroscopy. The latter absorption process may be slow compared to most chemical reactions. In considering potential energy curves for ground and excited electronic states of a diatomic molecule A—B comprised of atoms A and B, it is noted that horizontal lines usually represent vibrational energy levels. When energy is plotted on an ordinate scale and bond distance on an abscissa scale, a ground-state singlet to excited singlet can then be represented as $S_1$–$S_1$. With the absorption of a photon by paired electrons at a higher vibrational energy level the process may lead to a transition route 1 which raises the excited singlet state to an energy level leading to dissociation. A transition route 2 is now described wherein absorption of a photon at a lower vibrational energy level, where the bond radius is greater compared to the bond radius of paired electrons in transition route 1, results in raising the excited electronic state to an excitation level which first undergoes vibrational relaxation (usually represented by a wavy line). Subsequently, when the vibrational energy level reaches the lowest vibrational energy level for this excited state, a transition route F takes place which results in fluorescence. If prior to route F, the excited singlet $S_1$ achieves a cross over to the triplet state (which has its boundary curve defined by $T_1$), the vibrational relaxation (which is also represented by a wavy line) takes place to the lowest vibrational level. Subsequently, transition from this lowest vibrational state to the ground state is described as a transition route P which results in phosphorescence. The time for phosphorescence is the emission of light which continues for more than $10^{-8}$ seconds after excitation by radiation having a shorter wavelength, such as by electrons, ultraviolet light, or by X-rays. When emission of light occurs only during excitation with the luminescence ceasing within about $10^{-8}$ second after irradiation is stopped, the described occurrence is known as fluorescence. Reference is made to "Basic Principles of Organic Chemistry", Second Edition by Roberts and Caserio, page 1373, and particularly to FIG. 28-1 which is a schematic potential-energy diagram for ground and excited electronic states of a diatomic molecule A—A. This Figure wherein energy is plotted on ordinate scale and bond distance or abscissa scale depicts transmission F (fluorescence) and transition P (phosphorescence) as discussed hereinabove.

We claim:

1. An atmospheric contaminant detector system comprising:
   (i) an excitation source of a pulsed laser selected from the group consisting of a tripled Nd:Yag laser, a N$_2$ discharge laser, and a tunable dye laser to achieve excitation of an atmospheric contaminant in the form of dispersed gaseous molecules, said dispersed gaseous molecules being hazardous gas elements selected from the group consisting of chemical agents, nerve agents, and hazardous atmospheric pollutants, said excitation causing said dispersed gaseous molecules to be excited above ground state resulting in raising the electronic state to an excitational energy level which first undergoes vibrational relaxation by a transition route to the lowest vibrational energy level for said excited gaseous molecule where a transition route takes place while returning to a ground state which results in fluorescence as a result of emitting a photon at a measurable frequency to thereby determine the identify of said atmospheric contaminant;
   (ii) a digital controller having a means for firing said selected pulsed laser in direction of an atmospheric contaminant in the form of dispersed gaseous molecules, said digital controller also having means for determining the range and density of said excited gaseous molecules which fluoresces as a result of photo emission; and,
   (iii) a photo-detector having a plurality of notch filters in combination therewith which enables said photo-detector to detect more than one hazardous gas element or other atmospheric pollutant at a time by detecting each photon emission from each excited gaseous molecule returning to ground state, said photo-detector having an output which is subsequently transmitted to said digital controller which determines the distance and intensity of each of said photon emission via said photo-detector system.

2. The atmospheric contaminant detector system as defined in claim 1, wherein a timer in said system determines time elapse from the time said laser is pulsed to the time a photon is detected to thereby determine the distance of said photon emission.

3. The atmospheric contaminant detector system as defined in claim 2 wherein said digital controller includes means for determining distance of said photon emission which is correlated with intensity of fluorescence via said photo-detector to thereby determine density of said gaseous molecules in the atmosphere.

* * * * *